US008358824B2

(12) United States Patent
Hagiwara

(10) Patent No.: US 8,358,824 B2
(45) Date of Patent: Jan. 22, 2013

(54) X-RAY CT APPARATUS

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 586 days.

(21) Appl. No.: 12/652,634

(22) Filed: Jan. 5, 2010

(65) Prior Publication Data

US 2010/0172563 A1    Jul. 8, 2010

(30) Foreign Application Priority Data

Jan. 5, 2009  (JP) ................................. 2009-000138

(51) Int. Cl.
*G06K 9/00*    (2006.01)
(52) U.S. Cl. ........................................... 382/131; 378/4
(58) Field of Classification Search ................ 378/4–20; 382/131, 128
See application file for complete search history.

(56) References Cited

U.S. PATENT DOCUMENTS

| | | | |
|---|---|---|---|
| 4,789,929 A | 12/1988 | Nishimura et al. | |
| 5,224,135 A | 6/1993 | Toki | |
| 5,278,884 A | 1/1994 | Eberhard et al. | |
| 5,463,666 A | 10/1995 | Eberhard et al. | |
| 5,751,782 A | 5/1998 | Yoshitome | |
| 5,784,481 A | 7/1998 | Hu | |
| 6,154,515 A | 11/2000 | Lin et al. | |
| 6,907,100 B2 | 6/2005 | Taguchi | |
| 6,907,102 B1 | 6/2005 | Sauer et al. | |
| 6,990,170 B2 * | 1/2006 | Sugihara et al. | 378/15 |
| 7,173,997 B2 | 2/2007 | Hagiwara | |
| 2002/0037068 A1 | 3/2002 | Oikawa | |
| 2007/0291894 A1 * | 12/2007 | Hagiwara et al. | 378/4 |

FOREIGN PATENT DOCUMENTS

JP    2008-000168    1/2008

* cited by examiner

*Primary Examiner* — Hoon Song
(74) *Attorney, Agent, or Firm* — Armstrong Teasdale LLP

(57) ABSTRACT

An X-ray CT apparatus reconstructs a CT image (extended CT image) at each slice position lying outside a relative linear movement range at a helical scan or the like at low exposure and with high image quality. Scans each provided with a residence time are executed at relative linear movement start and end points (Zs and Zf). Projection data in a view range (F) corresponding to a predetermined view angle centering on a view (CVp1,zs) corresponding to a relative linear movement start time or a view shifted previously therefrom by the number of views (M), or a view (CVp1,zf) corresponding to a relative linear movement end time or a view shifted backward therefrom by the number of views (N) are used as image reconstruction projection data for extended CT images in image extension regions (Rs and Rf).

20 Claims, 12 Drawing Sheets

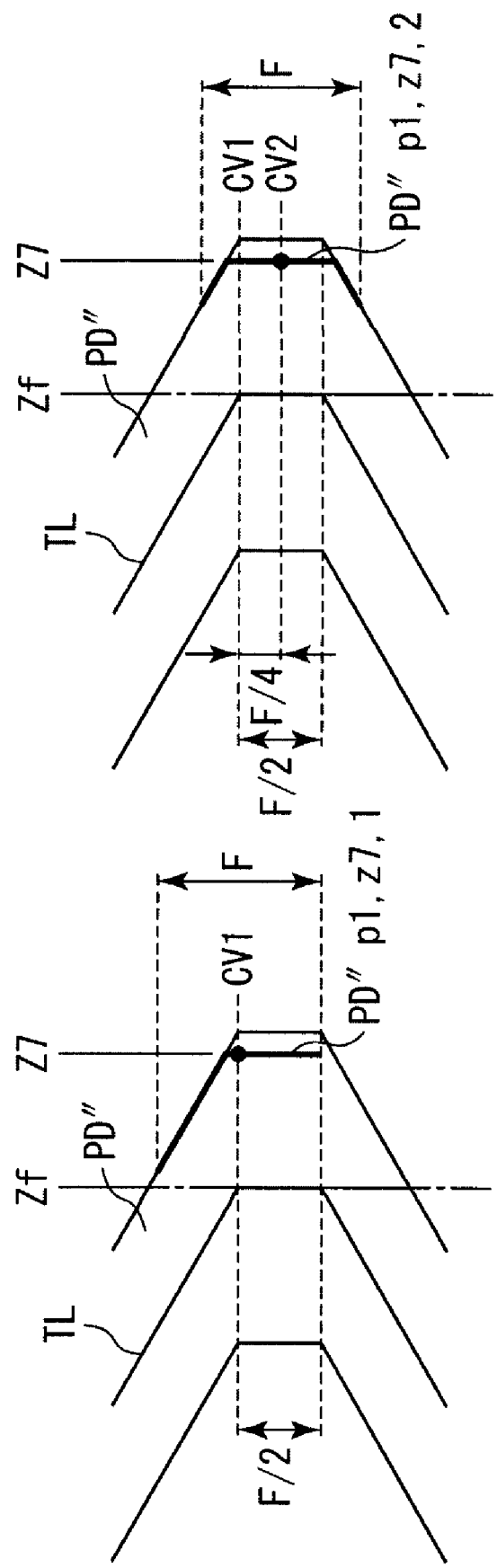

# X-RAY CT APPARATUS

CROSS REFERENCE TO RELATED APPLICATIONS

This application claims the benefit of Japanese Patent Application No. 2009-000138 filed Jan. 5, 2009, which is hereby incorporated by reference in its entirety.

BACKGROUND OF THE INVENTION

The embodiments described herein relate to an X-ray CT (Computed Tomography) apparatus.

As one imaging method using an X-ray CT apparatus, there has been known a so-called helical scan for relatively linearly moving an X-ray tube and an X-ray detector in the direction of a body axis of a subject while rotating them about the subject to thereby acquire projection data. There has also been known an imaging method provided with residence times, in which upon execution of the helical scan, the above rotation is executed but the relative linear movement is not executed at start and end points of relative linear movement of the X-ray tube and the X-ray detector (refer to, for example, Japanese Unexamined Patent Publication No. 2008-000168). According to this imaging method, projection data in a view range corresponding to a predetermined view angle for image-reconstructing a CT image (hereinafter called also "extended CT image") at each slice position lying outside a relative linear movement range can reliably be acquired. As a result, the extended CT image can be image-reconstructed with high quality. Incidentally, the predetermined view angle is of, for example, a π+fan angle of an X-ray beam, 2π or a 2π+fan angle.

BRIEF DESCRIPTION OF THE INVENTION

However, in order to reliably acquire the projection data for image-reconstructing the corresponding CT image at the outermost slice position in a region in which the image reconstruction of each CT image is enabled outside the relative linear movement range, the residence times taken to execute the above rotation at a rotational angle corresponding to the predetermined view angle must be provided and hence exposure to the subject increases.

With the foregoing in view, the present invention provides an X-ray CT apparatus capable of image-reconstructing a CT image at each slice position lying outwardly of a relative linear movement range at a helical scan, a helical shuttle scan (helical scan continuously executed while the orientation of relative linear movement of the helical scan is being repeatedly reversed), a variable pitch helical scan (helical pitch variable helical scan capable of acquiring projection data even during acceleration/deceleration of relative linear movement) or the like at low exposure and with high image quality.

In a first aspect, the present invention provides an X-ray CT apparatus comprising an X-ray tube, an X-ray detector having a plurality of detector rows, rotating device for rotating the X-ray tube and the X-ray detector about a body axis of a subject, relative linear moving device for relatively linearly moving the X-ray tube and the X-ray detector relative to the subject from a relative linear movement start point to a relative linear movement end point, scan device for acquiring projection data by executing a resident scan and a moving scan, wherein said resident scan is for acquiring projection data while executing said rotation at the relative linear movement start point and/or the relative linear movement end point without executing said relative linear movement and said moving scan is for acquiring projection data while executing the rotation and the relative linear movement within a relative linear movement range; and image reconstructing device for reconstructing CT images including at least one of a first image reconstructing and a second image reconstructing using the acquired projection data, wherein said first image reconstructing is for reconstructing a CT image at a slice position located outside the relative linear movement start point of the relative linear movement range, said CT image is reconstructed using projection data in a view range, said view range being corresponding to predetermined view angles, which view at the relative linear movement start time or its proximal view being in the center thereof, and including view based on the resident scan and view based on the moving scan, and when projection data for the image reconstruction lack, using existing projection data based on the moving scan contained in the view range as a substitute for the lacked projection data, and said second image reconstructing is for reconstructing a CT image at a slice position located outside the relative linear movement end point of a relative linear movement range, said CT image is reconstructed using projection data in a view range, said view range being corresponding to predetermined view angles, which view at the relative linear movement end time or its proximal view being in the center thereof, and including view based on the resident scan and view based on the moving scan, and when projection data for the image reconstruction lack, using existing projection data based on the moving scan contained in the view range as a substitute for the lacked projection data.

In a second aspect, the present invention provides the X-ray CT apparatus according to the first aspect, wherein the scan device sequentially executes the resident scan for executing the rotation at a rotational angle smaller than the predetermined view angle at the relative linear movement start point, and the moving scan, and wherein the image reconstructing device executes the first image reconstructing.

In a third aspect, the present invention provides the X-ray CT apparatus according to the first aspect, wherein the scan device sequentially executes the moving scan and the resident scan for executing the rotation at a rotational angle smaller than the predetermined view angle at the relative linear movement end point, and wherein the image reconstructing device executes the second image reconstructing.

In a fourth aspect, the present invention provides the X-ray CT apparatus according to the first aspect, wherein the scan device sequentially executes the moving scan, the resident scan executes the rotation at a rotational angle smaller than twice the predetermined view angle at the relative linear movement end point, and the moving scan by setting the relative linear movement end point to a new relative linear movement start point, and wherein the image reconstructing device executes image processing using the second image reconstructing and the first image reconstructing at the new relative linear movement start point.

In a fifth aspect, the present invention provides the X-ray CT apparatus according to any one of the first through fourth aspects, wherein each of the projection data used as the substitute for the lacked projection data is projection data lying in a view range of less than half the predetermined view angle.

In a sixth aspect, the present invention provides the X-ray CT apparatus according to any one of the first through fifth aspects, wherein the image reconstructing device reconstructs the CT image using projection data lying in a view range centering on a view located, by a first view number, temporally prior to the view corresponding to the relative linear movement start time in the first image reconstructing, and reconstructs the CT image using projection data lying in a view range centering on a view located, by a second view number, temporally subsequent to the view corresponding to the relative linear movement end time in the second image reconstructing.

In a seventh aspect, the present invention provides the X-ray CT apparatus according to the sixth aspect, wherein the first and second view numbers depend on one rotation time per rotation referred to above.

Incidentally, the feature of the X-ray CT apparatus according to the seventh aspect can also be considered to reside in that the first and second view numbers depend on the amount of the relative linear movement relative to the predetermined view angle.

In an eighth aspect, the present invention provides the X-ray CT apparatus according to the seventh aspect, wherein the first and second view numbers increase as the one rotation time becomes large.

In a ninth aspect, the present invention provides the X-ray CT apparatus according to the sixth aspect, wherein the first view number depends on a first length extending from the relative linear movement start point to the slice position at the outside on the relative linear movement start point side, and wherein the second view number depends on a second length extending from the relative linear movement end point to the slice position at the outside on the relative linear movement end point side.

In a tenth aspect, the present invention provides the X-ray CT apparatus according to the ninth aspect, wherein the first view number increases as the first length becomes large, and wherein the second view number increases as the second length becomes large.

In an eleventh aspect, the present invention provides the X-ray CT apparatus according to any one of the sixth through tenth aspects, wherein the second view number is smaller than the first view number.

In a twelfth aspect, the present invention provides the X-ray CT apparatus according to any one of the sixth through eleventh aspects, wherein the first and second view numbers are less than half the number of views corresponding to the predetermine view angle.

In a thirteenth aspect, the present invention provides the X-ray CT apparatus according to any one of the first through twelfth aspects, wherein the predetermined view angle is a π+fan angle of an X-ray beam, 2π or a 2π+the fan angle.

In a fourteenth aspect, the present invention provides the X-ray CT apparatus according to any one of the first through thirteenth aspects, wherein the velocity of the relative linear movement changes while acquiring projection data.

Incidentally, in the above configuration, the "relative linear movement" is indicative of the meaning including a case where a subject or a table with the subject placed thereon is linearly moved without linearly moving an X-ray tube and an X-ray detector in a state in which the subject is placed in between the X-ray tube and the X-ray detector, a case where the X-ray tube and the X-ray detector are linearly moved without linearly moving the subject or the table with the subject placed thereon, a case where the subject or the table with the subject placed thereon is linearly moved or the X-ray tube and the X-ray detector are linearly moved in an opposite direction, etc.

According to the present invention, a CT image at each slice position lying outwardly of a relative linear movement range is image-reconstructed using projection data in a view range corresponding to a predetermined view angle centering on a view corresponding to a relative linear movement start or finish time or its proximal view, and including each view based on a resident scan and each view based on a moving scan. When projection data necessary for image reconstruction lack at the image reconstruction, at least some of the projection data for the views based on the moving scan, contained in the view range are used instead of the lacked projection data. Correspondingly, a view range of projection data to be acquired by the resident scan can therefore be reduced while ensuring projection data lying in a view range effective in image reconstruction by a given amount. CT images at slice positions lying outwardly of a relative linear movement range at a helical scan, a helical shuttle scan, a variable pitch helical scan or the like can be image-reconstructed at low exposure and with high quality.

BRIEF DESCRIPTION OF THE DRAWINGS

FIGS. 12A and 12B are diagrams showing one example of image reconstruction projection data extracted where a residence time is made short.

DETAILED DESCRIPTION OF THE INVENTION

Embodiments of the present invention will hereinafter be described with reference to the accompanying drawings. Incidentally, the present invention is not limited to the present embodiments.

Figure 1:
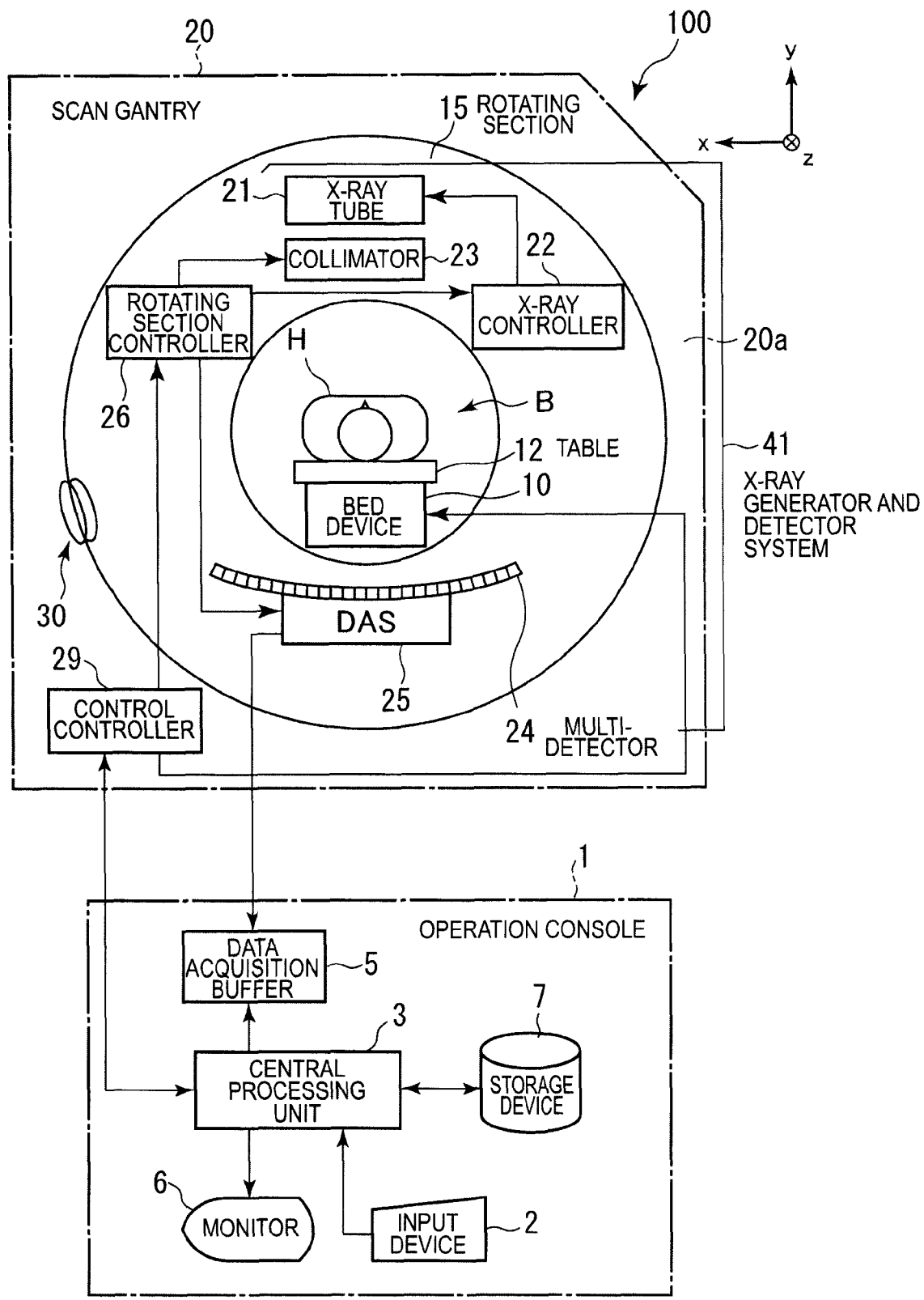
FIG. 1 is a configuration diagram showing an X-ray CT apparatus according to the present embodiment.

FIG. 1 is a configuration diagram showing an X-ray CT apparatus 100 according to the present embodiment.

The X-ray CT apparatus 100 is equipped with an operation console 1, a bed device (relative linear moving device) 10, and a scan gantry (rotating device) 20.

The operation console 1 is equipped with an input device 2 which accepts an input from a user, a central processing unit (image reconstructing device) 3 which executes an image reconstructing process, etc., a data acquisition buffer 5 which acquires projection data acquired by the scan gantry 20, a monitor 6 which displays each CT image subjected to image reconstruction, based on the projection data, and a storage device 7 which stores programs and data, and CT images therein.

The bed device 10 is equipped with a table 12 which places a subject H thereon and inserts and draws the subject H into and from a bore B of the scan gantry 20. The table 12 is elevated and linearly moved horizontally by a motor built in the bed device 10. Incidentally, in the present embodiment, the linear moving direction of the table 12 is assumed to be a z direction, its vertical direction is assumed to be a y direction, and its horizontal direction orthogonal to the z and y directions is assumed to be an x direction.

The scan gantry 20 has a rotating section 15 and a body section 20a which rotatably supports the rotating section 15. The rotating section 15 is provided with an X-ray tube 21, an X-ray controller 22 which controls the X-ray tube 21, a collimator 23 which shapes an X-ray beam radiated by the X-ray tube 21, a multidetector (X-ray detector) 24 provided in the z direction with a plurality of detector rows in which a plurality of X-ray detecting elements are disposed in a channel direction, a DAS (Data Acquisition System) 25 which converts outputs of the multidetector 24 to projection data and acquires them, and a rotating section controller 26 which controls the X-ray controller 22, collimator 23 and DAS 25. The body section 20a is equipped with a control controller 29 which performs transmission/reception of control signals or the like between the operation console 1 and the bed device 10. The rotating section 15 and the body section 20a are electrically coupled to each other via a slip ring 30.

The X-ray tube 21 and the multidetector 24 configure an X-ray data acquisition system or an X-ray generator and detector system 41. Here, the table 12 is linearly moved horizontally to cause the X-ray generator and detector system 41 to perform relative linear movement.

Incidentally, the scan gantry 20 and the central processing unit 3 are one example of scan device according to the present invention.

Thus, a data acquiring process executed by the X-ray CT apparatus 100 according to the present embodiment will be explained.

Figure 2:
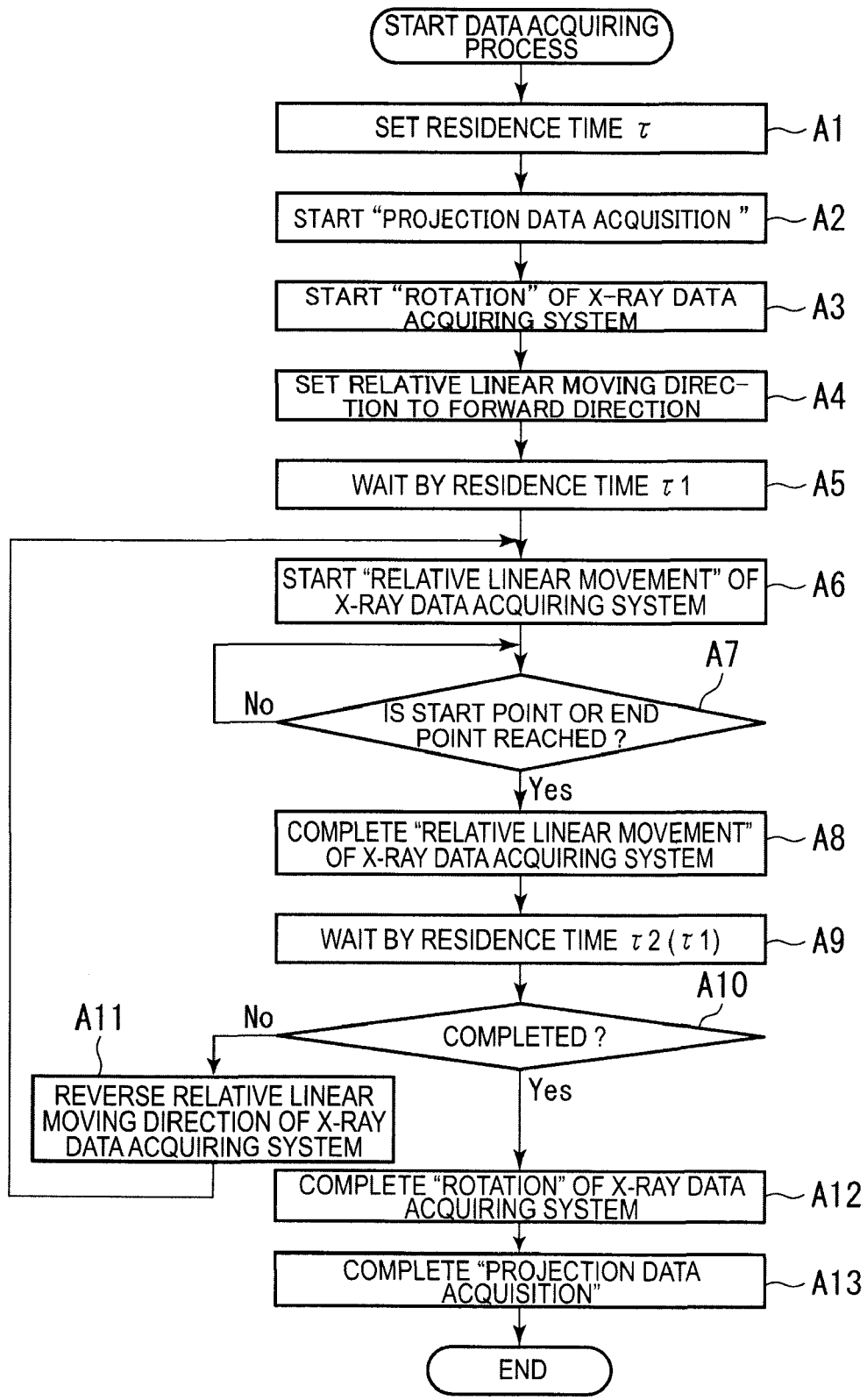
FIG. 2 is a flow diagram illustrating a data acquiring process according to the present embodiment.

FIG. 2 is a flow diagram showing the data acquiring process.

At step A1, a residence time t is set based on parameters set by the user as a scan condition.

One example of a method for setting the residence time t has been described from the 28th paragraph to the thirtieth paragraph of Japanese Unexamined Patent Publication No. 2008-000168. This setting method is of a method for setting residence times for reliably acquiring projection data corresponding to predetermined view angles necessary to perform image reconstruction on CT images in image extension regions. If the image reconstruction is assumed to be full reconstruction, for example, then a view angle F necessary for image reconstruction is taken as $2\pi$, and $\tau$ is set to $\tau=R-\{(W/2)-d\}/V$. If the image reconstruction is assumed to be half reconstruction, then a view angle necessary for image reconstruction is taken as $\pi$+fan angle ($\pi/3$, for example), and $\tau$ is set to $\tau=2R/3-\{(W/2)-d\}/V$. Here, R indicates time taken for one rotation of the rotating section 15 (one rotation time per rotation), W indicates a detector width (z-direction width of X-ray beam on rotational axis IC), d indicates an image extension region width on the side opposite to a relative linear moving direction (direction of forward path) as viewed from a relative linear movement start point Zs ($0<d\leq W/2$), and V indicates a relative linear moving velocity of the X-ray data acquiring 41.

Incidentally, now consider where a helical scan for causing the X-ray generator and detector system 41 to make at least one round or shuttle trip in a relative linear movement range Rm is executed. A CT image corresponding to a forward path for relative linear movement of the X-ray generator and detector system 41, and a CT image corresponding to a backward path therefor are separately image-reconstructed at the same slice position in the image extension region. Also consider where the amount of exposure to the subject H is more reduced compared with the above setting method.

Thus, the rotational angles of the X-ray generator and detector system 41 at the first and final resident scans are set smaller than the view angle F. The rotational angle of the X-ray generator and detector system 41 at a resident scan at the time of return of the relative linear movement of the X-ray generator and detector system 41 is set smaller than twice the view angle F.

As a concrete example, the image extension region width d=half W/2 of detector width and the image reconstruction is assumed to be the full reconstruction, i.e., the view angle F necessary for image reconstruction is assumed to be $2\pi$. Then, the rotational angles of the X-ray generator and detector system 41 at the first and final resident scans are assumed to be less than $2\pi$. That is, the first and final residence times are assumed to be $\tau 1<R$. The rotational angle of the X-ray generator and detector system 41 at the time of return of the relative linear movement of the X-ray generator and detector system 41 is assumed to be less than $4\pi$. Namely, the residence time (residence time other than the first and final resistance times) at the time of return of the relative linear movement of the X-ray generator and detector system 41 is assumed to be $\tau 2<2R$.

Figure 3:
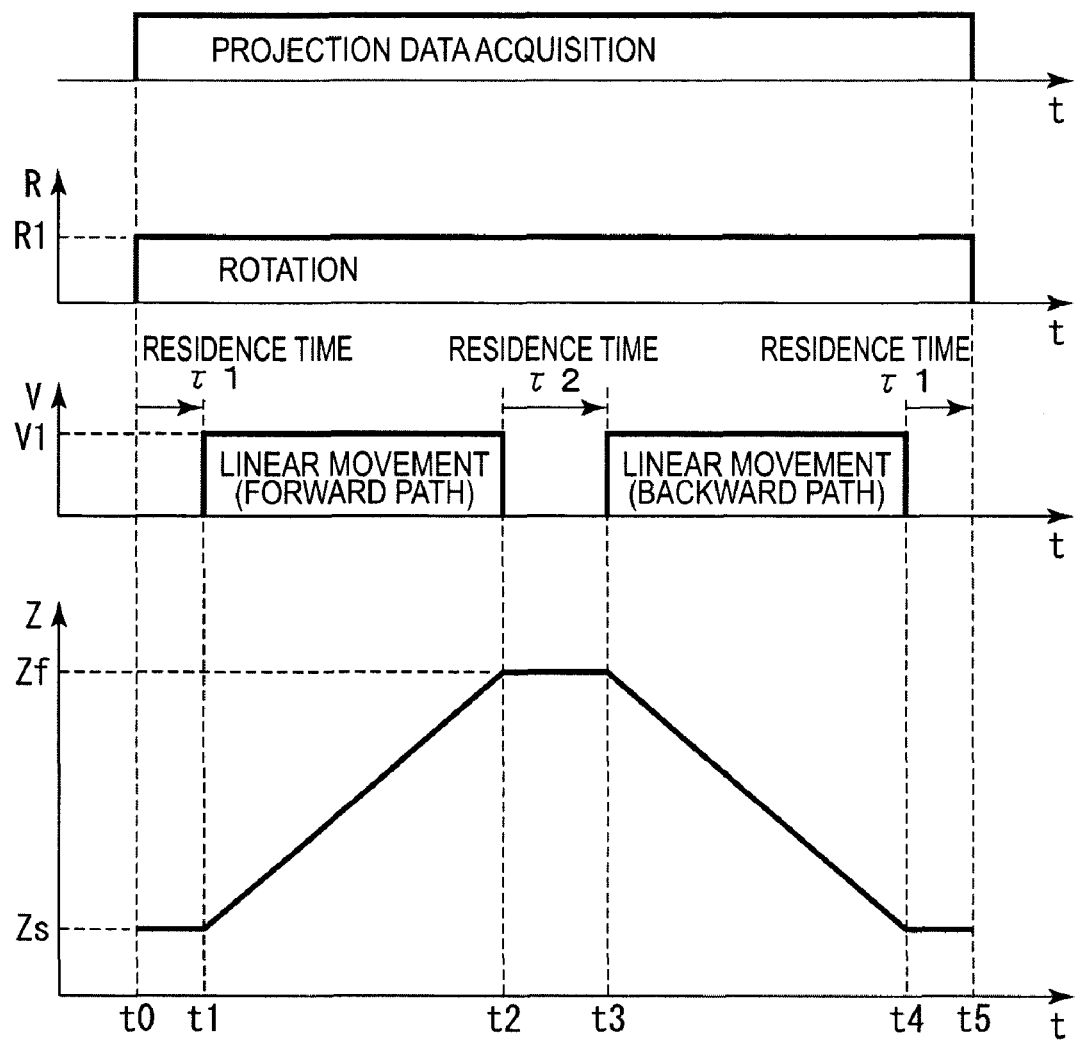
FIG. 3 is a time chart representing "projection data acquisition", "rotation", "relative linear movement", and "relative positions of X-ray tube and multidetector".

At step A2, "projection data acquisition" is started as indicated at a time t0 of FIG. 3, for example.

At step A3, "rotation" of the X-ray data acquiring system 41 is started as indicated at the time t0 of FIG. 3, for example.

At step A4, the direction (the relative linear moving direction of the X-ray generator and detector system 41) of movement of the table 12 is set to the forward-path direction (+z direction here).

At step A5, the X-ray data acquiring system 41 is caused to wait by the residence time $\tau 1$ as indicated at the times t0 to t1 of FIG. 3, for example. Namely, the X-ray data acquiring system 41 is caused to perform only rotation and acquires projection data only during the residence time $\tau 1$ without being caused to perform the relative linear movement (resident scan).

At step A6, the movement of the table 12 is started as indicated at a time t1 of FIG. 3, for example to thereby start the "relative linear movement" of the X-ray data acquiring system 41.

At step A7, the X-ray data acquiring system 41 is rotated and relatively linearly moved until the X-ray data acquiring system 41 reaches an end point Zf shown in FIG. 3, for example, to thereby acquire projection data (moving scan). When the X-ray data acquiring system 41 reaches the end point Zf indicated at a time t2 of FIG. 3, for example, the data acquiring process proceeds to step A8.

At step A8, the "relative linear movement" of the X-ray data acquiring system 41 is ended with the completion of the movement of the table 12 as indicated at the time t2 of FIG. 3, for example.

At step A9, the X-ray data acquiring system 41 is caused to wait by a residence time $\tau 2$ ($\tau 1$ if the final residence time is taken) as indicated at the times t2 to t3 of FIG. 3, for example. Namely, the X-ray data acquiring system 41 is caused to perform only rotation and acquires projection data only during the residence time τ2 (τ1) without being caused to perform the relative linear movement (resident scan).

At step A10, the data acquiring process proceeds to step A11 if intended data acquisition is not completed. If it is ended, then the data acquiring process proceeds to step A12.

At step A11, the direction (the direction of relative linear movement of the X-ray data acquiring system 41) of movement of the table 12 is reversed. Then, the data acquiring process returns to step A6, where the data acquisition is continued. Namely, projection data are acquired while the X-ray data acquiring system 41 is being moved relatively linearly in the direction opposite to the direction at the previous time with the previous end point taken as this start point and the previous start point taken as this end point (moving scan).

At step A12, the "rotation" of the X-ray data acquiring system 41 is completed as indicated at a time t4 of FIG. 3, for example.

At step A13, the "projection data acquisition" is ended as indicated at a time t5 of FIG. 3, for example.

Figure 4:
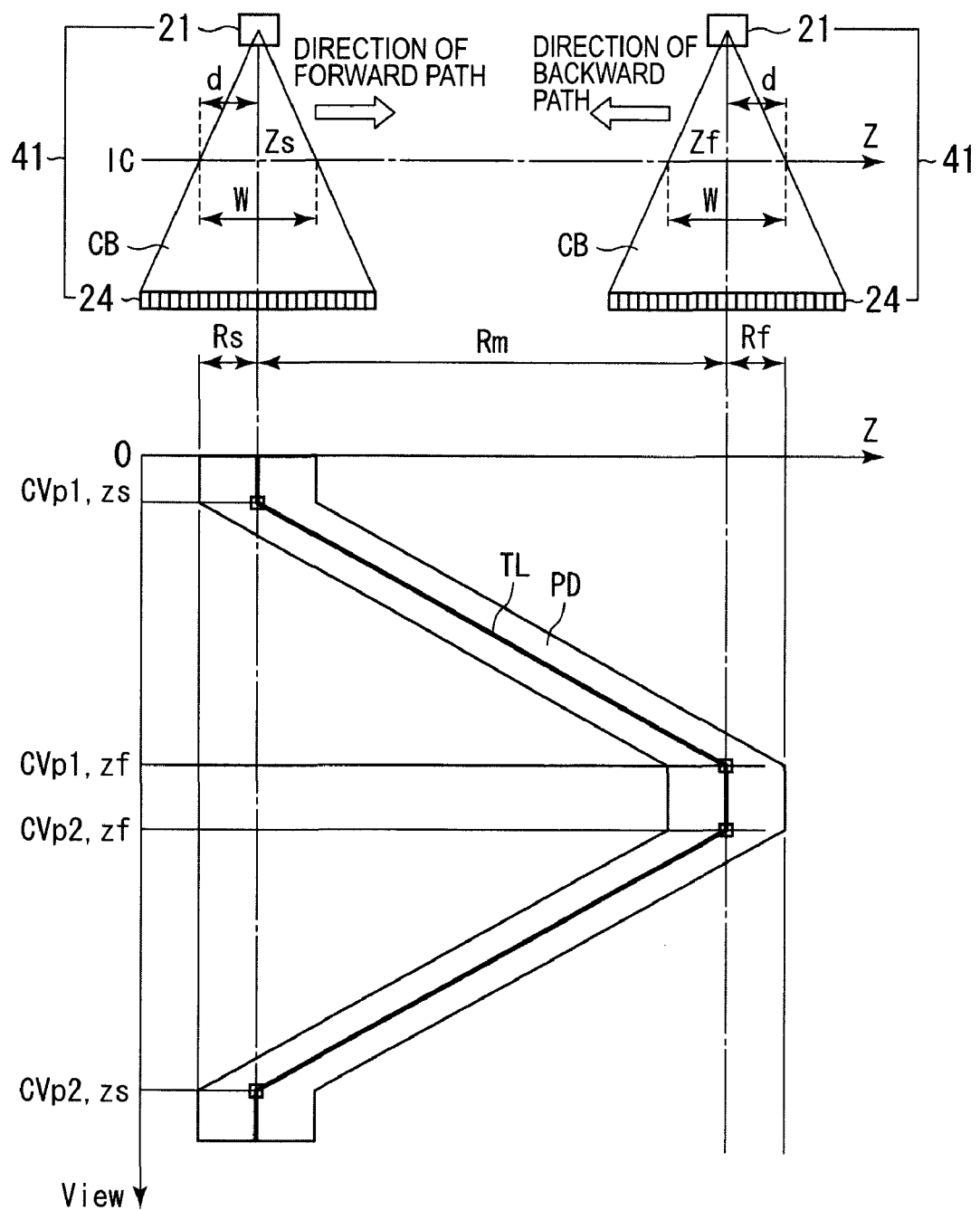
FIG. 4 is a diagram illustrating one example of projection data acquired by the data acquiring process according to the present embodiment.

FIG. 4 is a diagram typically showing projection data acquired by the data acquiring process. An upper stage of FIG. 4 typically shows the X-ray tube 21 and multidetector 24 that configure the X-ray data acquiring system 41 at a relative linear movement start time and a relative linear movement end time. A lower stage of FIG. 4 typically shows acquired projection data PD for all views. At the lower stage of FIG. 4, the horizontal axis indicates a position Z as viewed in the z direction of a reference position TL with respect to the subject H, of the X-ray data acquiring system 41, and the vertical axis indicates a view number View. Incidentally, the view number View is normally proportional to the time.

Thus, an image reconstructing process (first and second image reconstructing processes) executed by the X-ray CT apparatus 100 according to the present embodiment will be explained.

Figure 5:
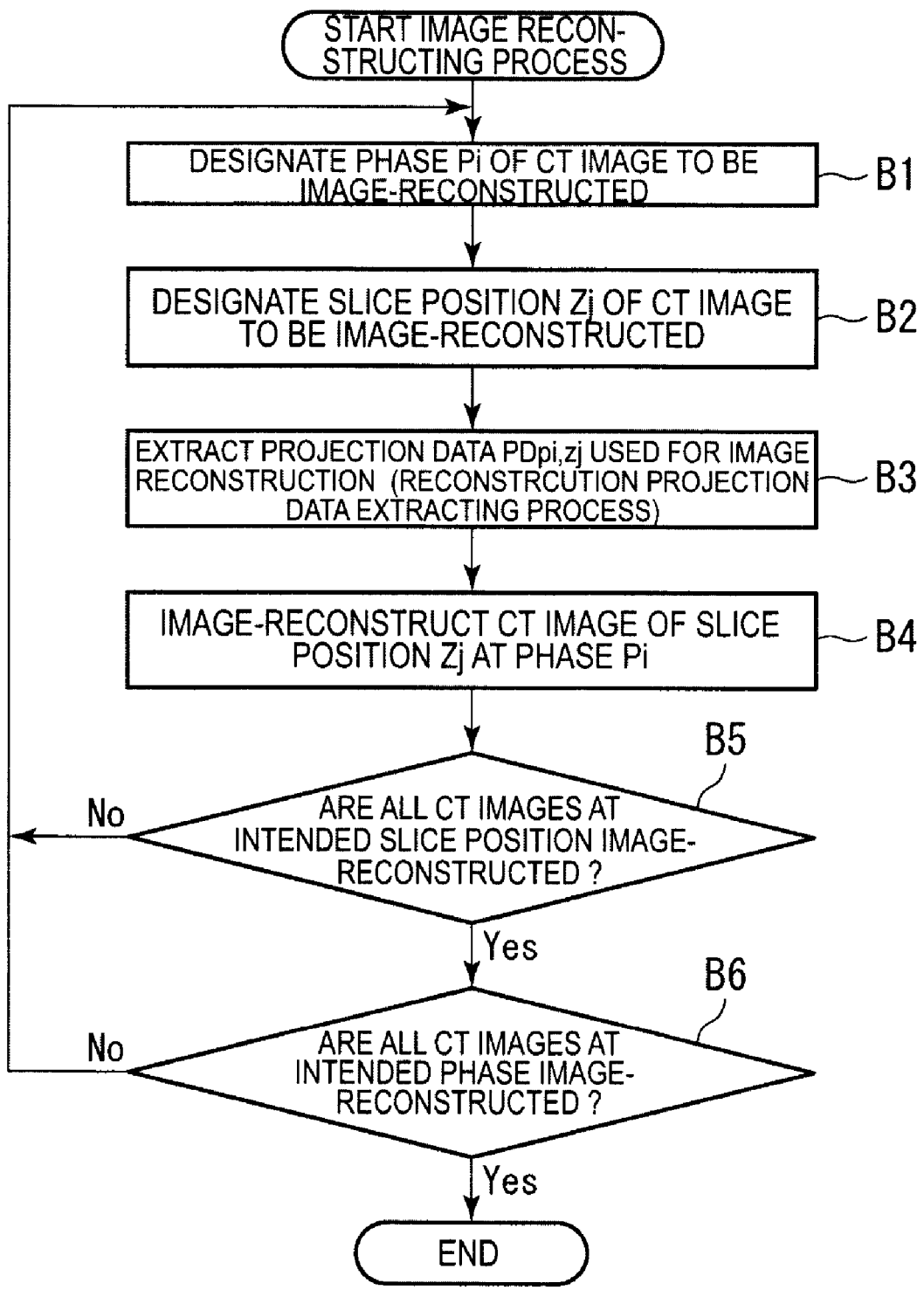
FIG. 5 is a flow diagram showing an image reconstructing process according to the present embodiment.

FIG. 5 is a flow diagram showing the image reconstructing process.

At step B1, a phase Pi of each CT image to be image-reconstructed is designated. Here, the phase Pi means the phase at the time that a helical scan is performed continuously. A first forward path, a first backward path, a second forward path, a second backward path . . . are respectively defined to become a phase P1, a phase P2, a phase P3, a phase P4 . . . . At step B1, the phases are designated one by one in time-series order each time step B1 is executed, for example. Incidentally, the user may set one or plural arbitrary phases or phase's ranges and sequentially designate the phases among them.

At step B2, a slice position Zj of the CT image to be image-reconstructed is designated. For example, all regions of an image extension region Rs on the relative linear movement start point Zs side, a relative linear movement range Rm and an image extension region Rf on the relative linear movement end point Zf side are assumed to be a slice position set region. Each time step B2 is executed, slice positions are sequentially designated at predetermined slice intervals in the z direction as viewed from the end of the slice position set region. Incidentally, the user may set one or plural arbitrary slice positions or slice ranges and sequentially designate the same among them.

At step B3, each projection data PDpi,zj used to image-reconstruct the CT image for the slice position Zj at the phase Pi is extracted. The process of extracting projection data used for the image reconstruction of each CT image will be explained in detail later.

At step B4, the CT image of the slice position Zj at the phase Pi is image-reconstructed using the extracted projection data PDpi,zj.

It is determined at step B5 whether the image reconstruction of the CT image is completed with respect to each intended slice position. If it is found not to have been completed, then the data acquiring process proceeds to step B3. If it is found to have been completed, then the data acquiring process proceeds to step B6.

It is determined at step B6 whether the image reconstruction of each CT image is completed with respect to the intended phase. If it is found not to have been completed, then the data acquiring process proceeds to step B1. If it is found to have been completed, then the image reconstructing process is ended.

The process of extracting projection data used for image reconstruction of each CT image will now be described in detail.

First Embodiment

Figure 6:
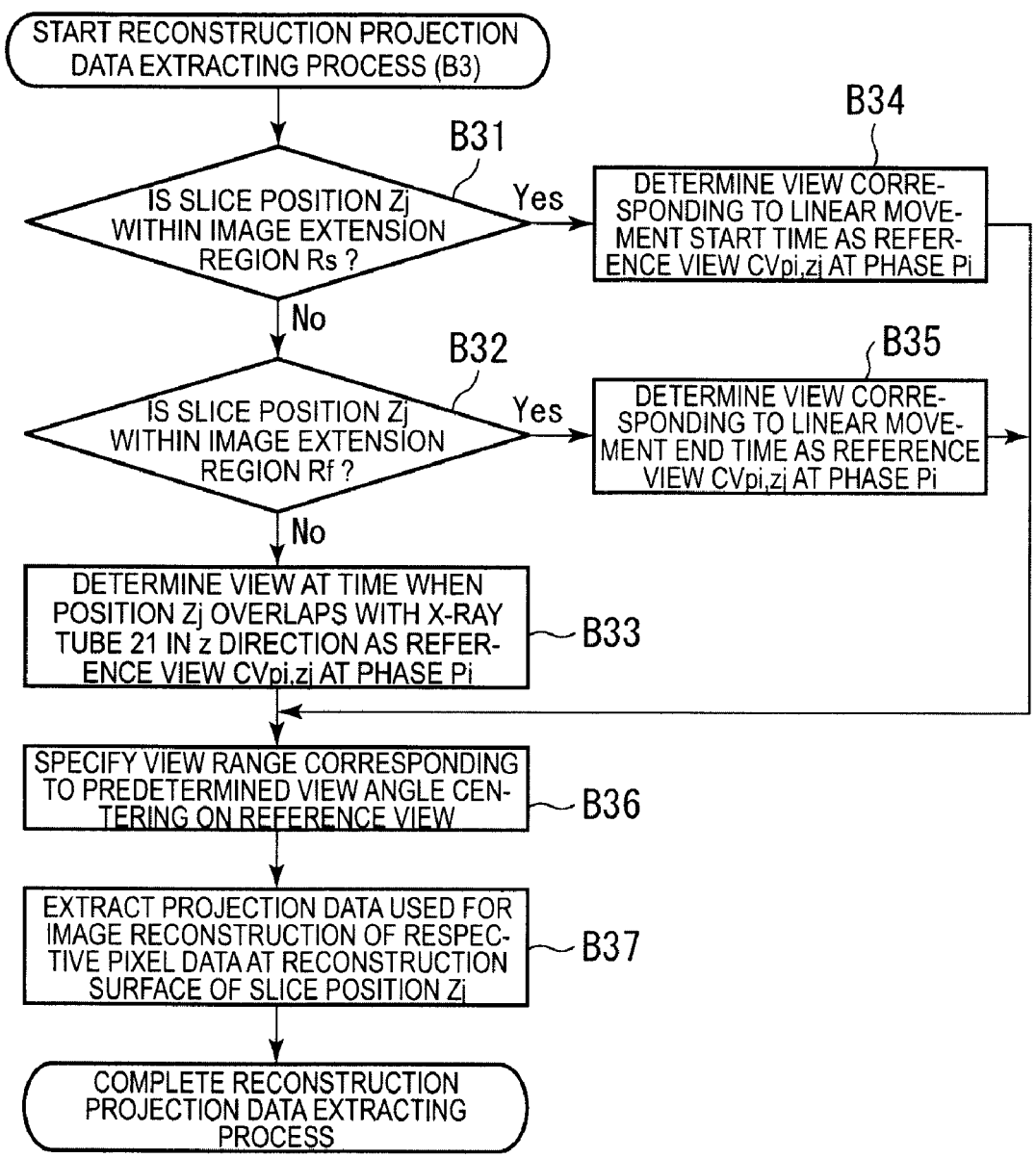
FIG. 6 is a flow diagram showing a process for extracting reconstruction projection data by a first method according to the present embodiment.

FIG. 6 is a flow diagram showing one example of a process for extracting reconstruction projection data by a first method.

It is determined at step B31 whether the slice position Zj falls within the image extension region Rs. If it is determined that the slice position Zj falls within the image extension region Rs, then the process proceeds to step B34. If not so, then the process proceeds to step B32.

It is determined at step B32 whether the slice position Zj falls within the image extension region Rf. If it is determined that the slice position Zj falls within the image extension region Rf, then the process proceeds to step B35. If not so, then the process proceeds to step B33.

At step B33, a view of projected data acquired at a time when the slice position Zj at the phase Pi and the reference position TL relative to the subject H, of the X-ray data acquiring system 41 coincide with each other in the z direction, is determined as a reference view CVpi,zj, and the process proceeds to step B36. The reference position TL of the X-ray data acquiring system 41 corresponds to, for example, the position of a point where a straight line formed by connecting an X-ray focal point of the X-ray tube 21 and the center of the multidetector 24, and the rotational axis IC of the X-ray data acquiring system 41 intersect.

On the other hand, at step B34, a view CVpi,zs of projection data acquired at the relative linear movement start time is determined as a reference view CVpi,zj at the relative linear movement start point Zs at the phase Pi, and the process proceeds to step B36.

At step B35, a view CVpi,zf of projection data acquired at the relative linear movement end time is determined as a reference view CVpi,zj at the relative linear movement end point Zf at the phase Pi, and the process proceeds to step B36.

At step B36, a view range VRpi,zj corresponding to a predetermined view angle F with the reference view CVpi,zj taken as the center is specified. The predetermined view angle F becomes $2\pi$ or $2\pi$+fan angle of an X-ray beam when the image reconstruction is taken as the full reconstruction. When the image reconstruction is taken as the half reconstruction, the predetermined view angle F becomes $\pi$+fan angle of the X-ray beam. The fan angle is $\pi/3$, for example.

At step B37, projection data in respective view directions to be back-projected for the purpose of image reconstruction of data of respective pixels on a reconstruction surface of a slice position Zj are extracted with respect to the respective pixels from within projection data corresponding to plural detector rows at the view range VRpi,zj specified at step B36. For example, projection data each based on an X-ray beam that passes through each pixel to be image-reconstructed or its near position are extracted with respect to respective view directions corresponding to a view angle F.

There is however a case where when the slice position Zj falls within the image extension regions Rs and Rf, some of the projection data to be back-projected onto the reconstruction surface do not exist within the projection data in the view range VRpi,zj. Namely, when it is considered that pixel data of a given pixel lying on the reconstruction surface is image-reconstructed, at least some of projection data in the respective view directions used for its image reconstruction, i.e., projection data (hereinafter called "target projection data") based on the X-ray beam that passes through the pixel and its proximal position may lack without existing in the projection data of the view range VRpi,zj. At this time, projection data considered to be closest to the lacking target projection data is extracted instead from within the projection data in the view range VRpi,zj. For example, projection data whose view direction is approximately identical to its lacked target projection data and whose X-ray beam path (hereinafter called "path") is closest to the lacked target projection data is extracted instead of the lacked target projection data.

Substitutes for the projection data will now be explained in further detail.

When the slice position Zj falls within the image extension regions Rs and Rf, the view range corresponding to the predetermined view angle F centering on the view corresponding to each of the relative linear movement start time and the relative linear movement end time is specified as a view range used to image-reconstruct the CT image of the slice position Zj as described above. In doing so, the more the slice position Zj comes off from the relative linear movement start point Zs or the relative linear movement end point Zf within the image extension region, the narrower the view range including the target projection data within the specified view range. Depending on the slice position Zj, the specified view range cannot ensure a view range corresponding to a predetermined view angle F including all of target projection data, so that some of the target projection data lack.

Figure 7:
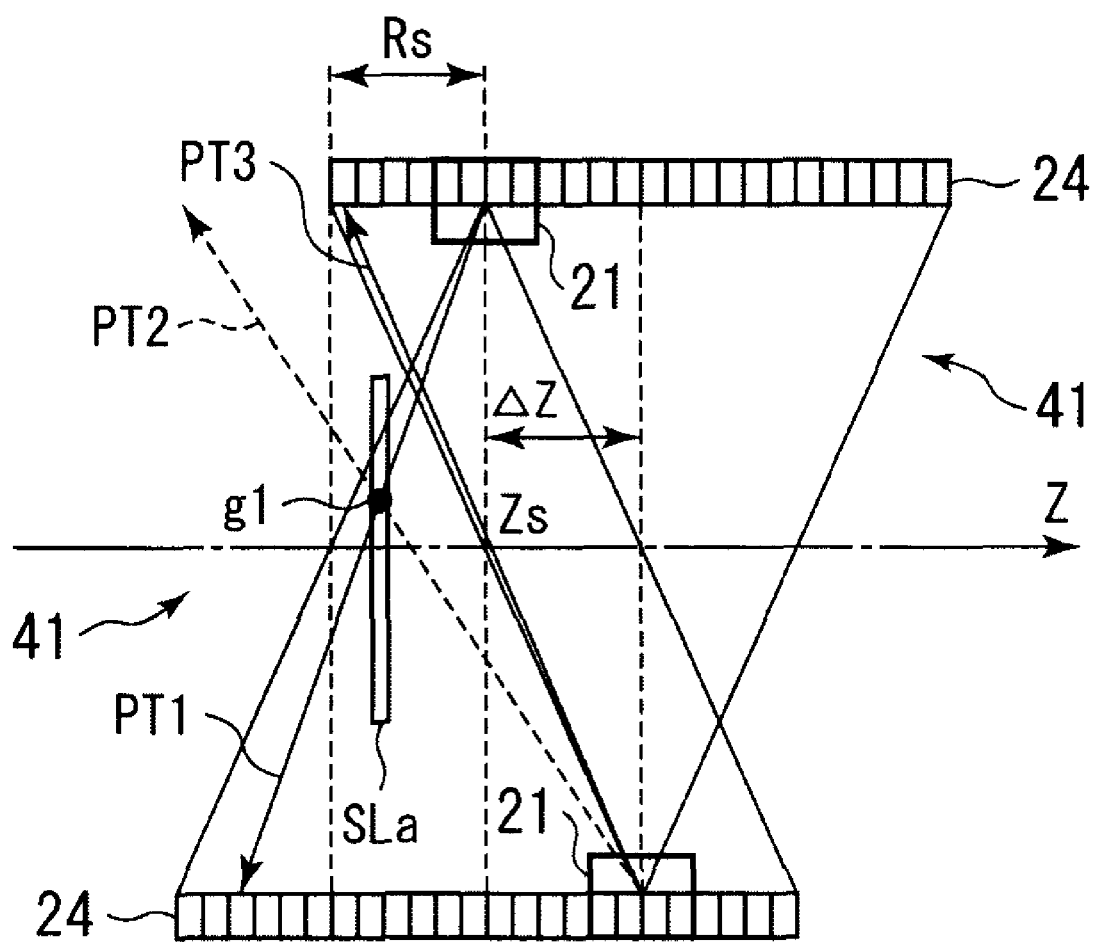
FIG. 7 is a diagram for describing a state in which projection data opposite in view direction are not acquired.

Consider where as shown in FIG. 7, for example, a pixel g1 of a slice SLa lying within an image extension region Rs is image-reconstructed.

Here, the specified view range indicates a view range corresponding to a predetermined view angle F with a view corresponding to a relative linear movement start time ta being taken as the center and comprises a view range based on a resident scan executed between a time to and the relative linear movement start time ta, and a view range based on a moving scan executed between the relative linear movement start time ta and a time tb after a predetermined time has elapsed.

Target projection data necessary to image-reconstruct the pixel g1 corresponds to projection data based on an X-ray beam that passes through a path extending through the pixel g1. Of projection data acquired at the relative linear movement start time ta, projection data of a path PT1 that passes through the pixel g1 is of target projection data. Projection data opposite in view direction to the projection data of the path PT1 also corresponds to target projection data. If it is not possible to acquire the corresponding projection data during the resident scan from the time to to the time ta, the projection data must be acquired during the moving scan from the time ta to the time tb.

Assume now that, for example, the X-ray data acquiring system 41 is rotated by a rotational angle $\pi$ within an xy plane by the moving scan and relatively linearly moved by a distance $\Delta Z$ in a z direction. If done so, projection data of a path PT2 opposite to the projection data of the path PT1 in the view direction is not collected in the projection data acquired at the time tb, and the projection data lacks the projection data of the path PT2. In this case, projection data of a path PT3 closest to the path PT2, of the projection data acquired at the time tb is extracted as an alternative to the lacked projection data of path PT2.

Even though the slice position of each CT image to be image-reconstructed is located in the outermost part within the image extension region if the rotational angle of the X-ray data acquiring system 41 at the resident scan is set more than being constant, necessary projection data can be prevented from lacking and the quality of the CT image can be prevented from deteriorating. This however increases the amount of exposure to the subject H. On the other hand, the method of the present embodiment more reduces the view range by the resident scan, of the view ranges used for the image reconstruction. Thus, even though the target projection data necessary for the image reconstruction may lack partly, the projection data close to the lacked target projection data is found out from within the projection data lying within the view range based on the moving scan and used as an alternative thereto. It is therefore possible to suppress deterioration in the quality of each CT image while suppressing the amount of exposure to the subject H. Namely, the CT image at each slice position lying outside the relative linear movement range can be image-reconstructed at low exposure and with high quality.

Incidentally, the projection data used as an alternative to the lacked projection data may preferably be set to projection data in a view range equivalent to less than half the predetermined view angle F. This is because when an excessive lot of projection data are substituted therefor, deterioration in the quality of each CT image to be image-reconstructed cannot be ignored.

Figure 8:
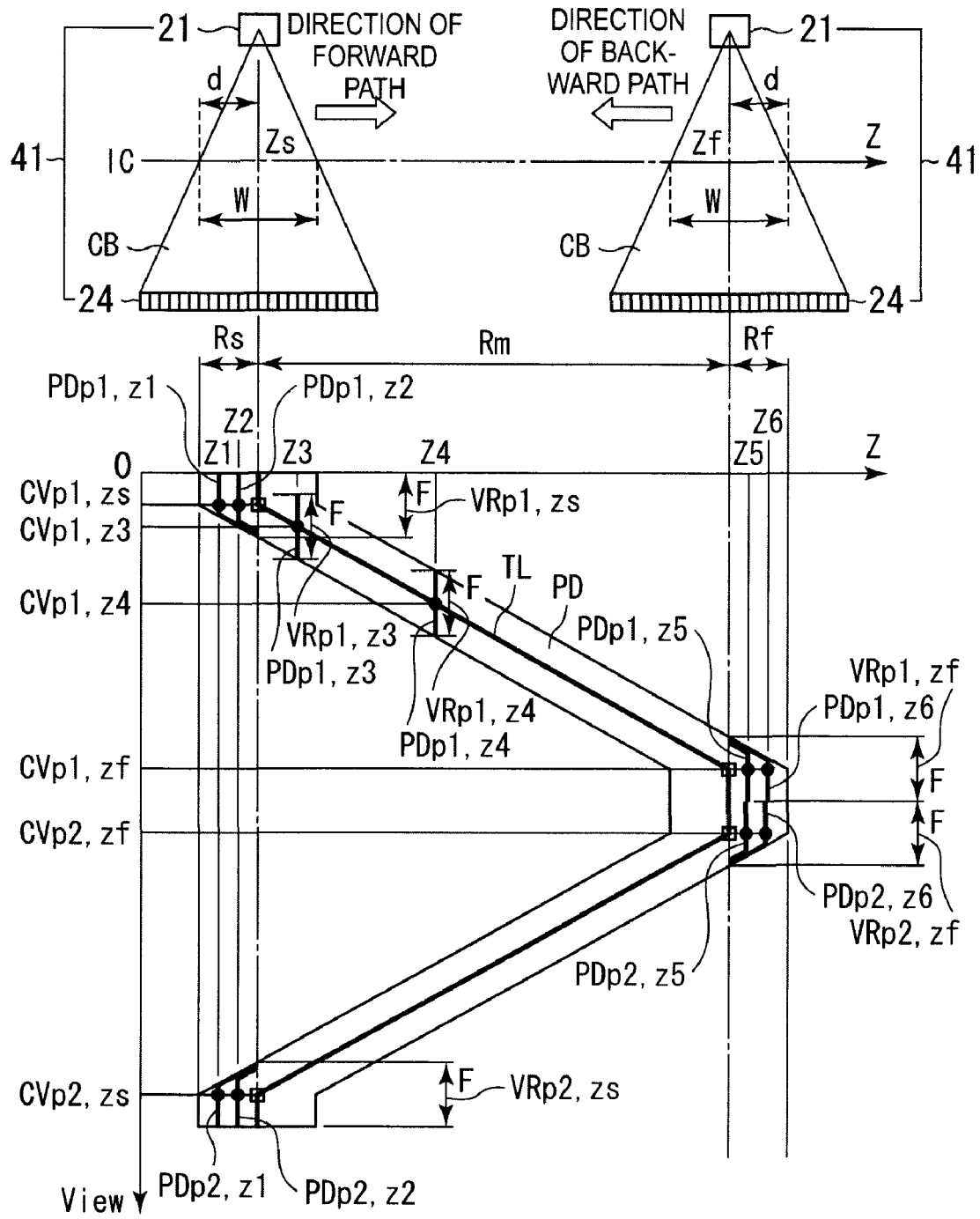
FIG. 8 is a diagram illustrating one example of projection data for image reconstruction extracted by the first method according to the present embodiment.

Projection data used for image reconstruction are extracted by the first method as shown in FIG. 8, for example.

As shown in FIG. 8, for example, a view CVp1,zs corresponding to a relative linear movement start time is taken as a reference view at a relative linear movement start point Zs with respect to slice positions Z1 and Z2 lying within an image extension region Rs at a phase P1. Then, view ranges VRp1,z1 (=VRp1,zs) and VRp1,z2 (=VRp1,zs) corresponding to a view angle F (2$\pi$, for example) with the reference view taken as the center are specified. Projection data PDp1,z1 and PDp1,z2 used for image reconstruction are respectively extracted from within projection data in the specified view ranges VRp1,z1 and VRp1,z2. In FIG. 8, longitudinal linear portions of the extracted projection data are target projection data, and oblique line portions thereof are substitute projection data near the target projection data.

In the case of slice positions Z3 and Z4 lying within a relative linear movement range Rm at the phase P1, views CVp1,z3 and CVp1,z4 corresponding to the respective slice positions at the phase P1 are taken as reference views. Then, view ranges VRp1,z3 and VRp1,z4 each corresponding to a view angle F with the reference view taken as the center are specified. Projection data PDp1,z3 and PDp1,z4 used for image reconstruction are respectively extracted from within projection data in the specified view ranges VRp1,z3 and VRp1,z4.

In the case of slice positions Z5 and Z6 lying within an image extension region Rf at the phase P1, a view CVp1,zf corresponding to a relative linear movement end time is taken as a reference view at a relative linear movement end point Zf at the phase P1. Then, view ranges VRp1,z5 and VRp1,z6 corresponding to a view angle F with the reference view taken as the center are specified. Projection data PDp1,z5 and PDp1,z6 used for image reconstruction are respectively extracted from within projection data in the specified view ranges VRp1,z5 and VRp1,z6.

In the case of the slice positions Z5 and Z6 lying within the image extension region Rf at a phase P2, a view CVp2,zf corresponding to a relative linear movement start time is taken as a reference view at its corresponding relative linear movement start point Zf at the phase P2. Then, view ranges VRp2,z5 (=VRp2,zf) and VRp2,z6 (=VRp2,zf) each corresponding to a view angle F with the reference view taken as the center are specified. Projection data PDp2,z5 and PDp2,z6 used for image reconstruction are respectively extracted from within projection data in the specified view ranges VRp2,z5 and VRp2,z6.

In the case of the slice positions Z1 and Z2 lying within the image extension region Rs at the phase P2, a view CVp2,zs corresponding to a relative linear movement end time is taken as a reference view at its corresponding relative linear movement end point Zs at the phase P2. Then, view ranges VRp2,z1 (=VRp2,zs) and VRp2,z2 (=VRp2,zs) each corresponding to a view angle F with the reference view taken as the center are specified. Projection data PDp2,z1 and PDp2,z2 used for image reconstruction are respectively extracted from within projection data in the specified view ranges VRp2,z1 and VRp2,z2.

According to the first method, it is possible to extract the projection data used for the image reconstruction, based on the easy-to-detect views corresponding to the relative linear movement start time and the relative linear movement end time. A program for the reconstruction projection data extracting process can therefore be simplified. The view range for the whole projection data used for the image reconstruction can be taken wide while suppressing the use of the projection data acquired at the resident scan, the amount of exposure to the subject can be reduced, and deterioration in the quality of each CT image can be suppressed. Although the times corresponding to the CT images in the image extension regions on the same side at one of the adjacent phases approach each other between the adjacent phases in the case of a helical shuttle, the time interval between the times can be made longer and hence an image desirable as a time-series image can be obtained.

Second Embodiment

In a second method, an adjustment for shifting a view range used for image reconstruction of each CT image to the view side of a resident scan by a predetermined amount is added on the basis of the first method in such a manner that the difference between a path for substitute projection data and its target path becomes small. Namely, when a slice position Zj falls within an image extension region Rs, each view shifted previously in time by the number of views M (first view number) from a view CVpi,zs of projection data acquired at a relative linear movement start time at a relative linear movement start point Zs at the same phase Pi is determined as a reference view CVpi,zj. When the slice position Zj falls within an image extension region Rf, each view shifted backward in time by the number of views N (second view number) from a view CVpi,zf of projection data acquired at a relative linear movement end time of a relative linear movement end point Zf at the same phase Pi is determined as a reference view CVpi,zj.

Figure 9:
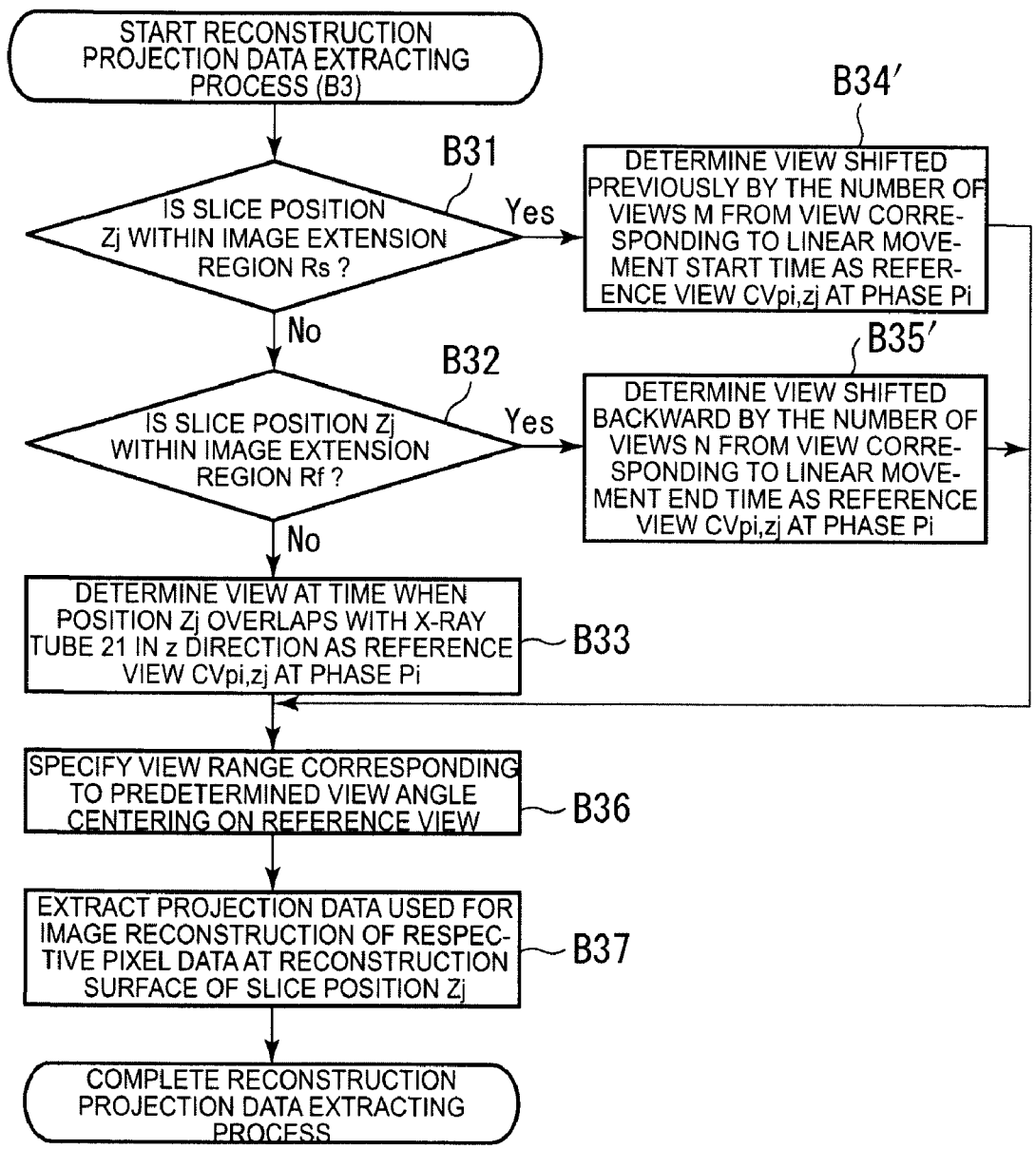
FIG. 9 is a flow diagram showing a reconstruction projection data extracting process executed by a second method according to the present embodiment.

FIG. 9 is a flow diagram showing one example of a process for extracting reconstruction projection data by the second method.

It is determined at step B31 whether the slice position Zj falls within the image extension region Rs. If it is determined that the slice position Zj falls therewithin, then the process proceeds to step B34'. If not so, then the process proceeds to step B32.

It is determined at step B32 whether the slice position Zj falls within the image extension region Rf. If it is determined that the slice position Zj falls therewithin, then the process proceeds to step B35'. If not so, then the process proceeds to step B33.

At step B33, a view of projected data acquired at a time when the slice position Zj at a phase Pi and a reference position TL relative to the subject H, of the X-ray data acquiring system 41 coincide with each other in the z direction, is determined as a reference view CVpi,zj, and the process proceeds to step B36.

On the other hand, at step B34', a view shifted previously in time by the number of views M from a view CVpi,zs of projection data acquired at a relative linear movement start time at a relative linear movement start point Zs at the phase Pi is determined as a reference view CVpi,zj, and the process proceeds to step B36. Incidentally, the number of views M is normally less than half the number of views equivalent to a view angle F.

At step B35', a view shifted backward in time by the number of views N from a view CVpi,zf of projection data acquired at a relative linear movement end time at a relative linear movement end point Zf at the phase Pi is determined as a reference view CVpi,zj, and the process proceeds to step B36. Incidentally, the number of views N is normally less than half the number of views equivalent to the view angle F.

At step B36, a view range VRpi,zj corresponding to a predetermined view angle F with the reference view CVpi,zj taken as the center is specified.

At step B37, projection data in respective view directions to be back-projected for the purpose of image reconstruction of data of respective pixels on a reconstruction surface of the slice position Zj are extracted with respect to the respective pixels from within projection data corresponding to plural detector rows in the view range VRpi,zj specified at step B36. When no target projection data exists, projection data considered to be closest to the target projection data is extracted instead from within the projection data in the view range VRpi,zj.

Figure 10:
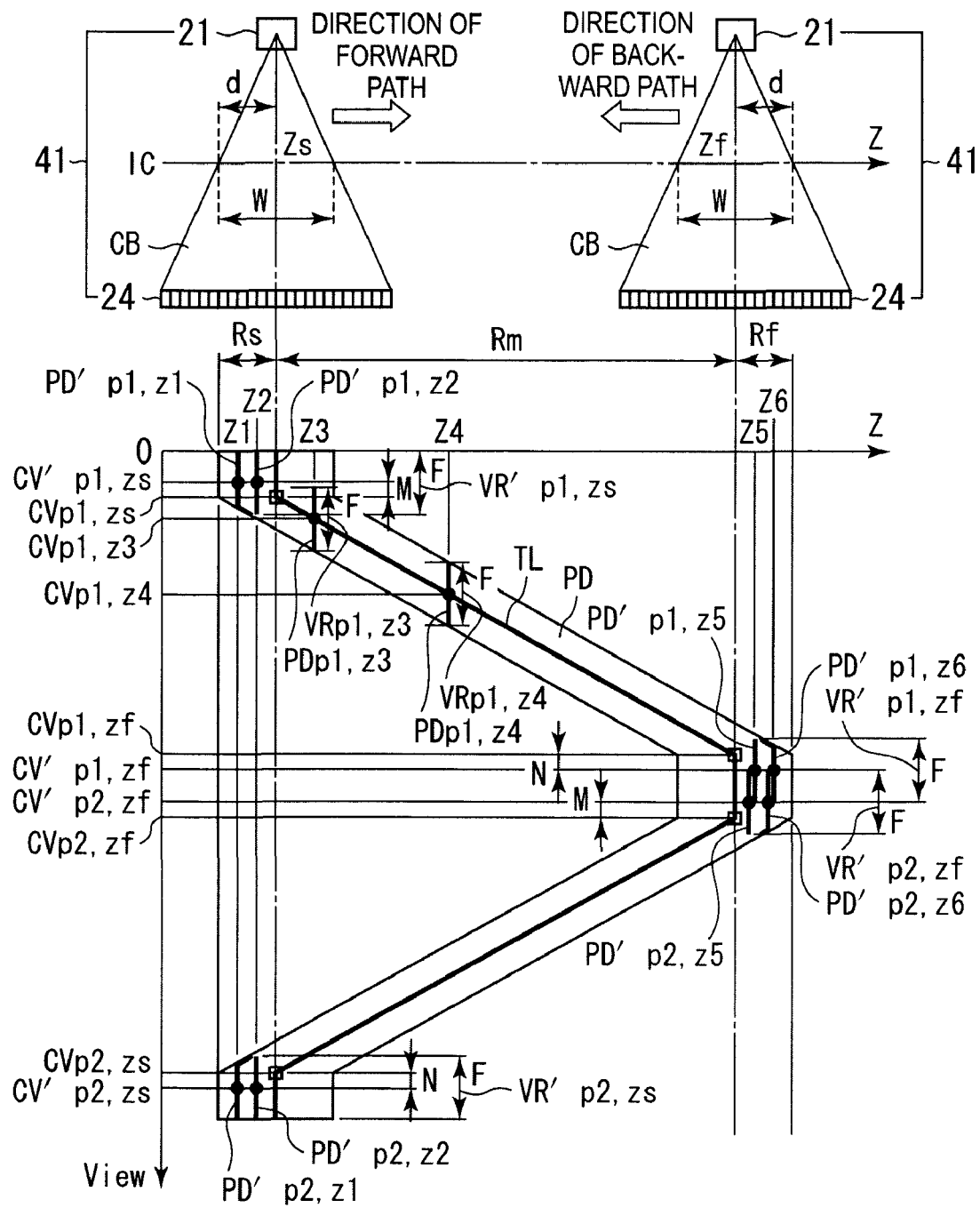
FIG. 10 is a diagram depicting one example of projection data for image reconstruction extracted by the second method according to the present embodiment.

Projection data used for image reconstruction are extracted by the second method as shown in FIG. 10, for example.

As shown in FIG. 10, for example, a view CV'p1,zs shifted previously in time by the number of views M from a view CVp1,zs corresponding to a relative linear movement start time at a relative linear movement start point Zs at a phase P1 is taken as a reference view with respect to slice positions Z1 and Z2 lying within an image extension region Rs at the phase P1. Then, view ranges VR'p1,z1 (=VR'p1,zs) and VR'p1,z2 (=VR'p1,zs) corresponding to a view angle F centering on the reference view are specified. Projection data PD'p1,z1 and PD'p1,z2 used for image reconstruction are respectively extracted from within projection data in the specified view ranges VR'p1,z1 and VR'p1,z2. In FIG. 10, longitudinal linear portions of the extracted projection data are target projection data, and oblique line portions thereof are substitute projection data near the target projection data.

In the case of slice positions Z3 and Z4 lying within a relative linear movement range Rm at the phase P1, views CVp1,z3 and CVp1,z4 corresponding to the respective slice positions at the phase P1 are taken as reference views. Then, view ranges VRp1,z3 and VRp1,z4 each corresponding to a view angle F with the reference view taken as the center are specified. Projection data PDp1,z3 and PDp1,z4 used for image reconstruction are respectively extracted from within projection data in the specified view ranges VRp1,z3 and VRp1,z4.

In the case of slice positions Z5 and Z6 lying within an image extension region Rf at the phase P1, a view shifted backward in time by the number of views N from a view CVp1,zf corresponding to a relative linear movement end time at a relative linear movement end point Zf at the phase P1 is taken as a reference view CV'p1,zf. Then, view ranges VR'p1,z5 and VR'p1,z6 corresponding to a view angle F centering on the reference view are specified. Projection data PD'p1,z5 and PD'p1,z6 used for image reconstruction are respectively extracted from within projection data in the specified view ranges VR'p1,z5 and VR'p1,z6.

In the case of the slice positions Z5 and Z6 lying within the image extension region Rf at a phase P2, a view CV'p1,zf shifted previously in time by the number of views M from a CVp1,zf corresponding to a relative linear movement start time at the relative linear movement start point Zf at the phase P2 is taken as a reference view. Then, view ranges VR'p2,z5 (=VR'p2,zf) and VR'p2,z6 (=VR'p2,zf) each corresponding to a view angle F with the reference view taken as the center are specified. Projection data PD'p2,z5 and PD'p2,z6 used for image reconstruction are respectively extracted from within projection data in the specified view ranges VR'p2,z5 and VR'p2,z6.

In the case of the slice positions Z1 and Z2 lying within the image extension region Rs at the phase P2, a view CV'p2,zs shifted backward in time by the number of views N from a view CVp2,zs corresponding to a relative linear movement end time at the relative linear movement end point Zs at the phase P2 is taken as a reference view. Then, view ranges VR'p2,z1 (=VR'p2,zs) and VR'p2,z2 (=VR'p2,zs) each corresponding to a view angle F with the reference view taken as the center are specified. Projection data PD'p2,z1 and PD'p2,z2 used for image reconstruction are respectively extracted from within projection data in the specified view ranges VR'p2,z1 and VR'p2,z2.

According to the second method, a path for substitute projection data is made closer to a path for target projection data to reduce inconsistency at image reconstruction, thereby making it possible to more suppress deterioration in the quality of each CT image. Incidentally, for example, when the residence time τ is small with respect to the rotational velocity of the scan gantry 20, when the moving velocity V of the table 12 is larger than that, and when the slice positions lying within the image extension regions Rs and Rf are separated from the relative linear movement start point Zs and the relative linear movement end point Zf, there is a strong tendency that the distance between the path for the target projection data and the path for the substitutable projection data increases greatly. The second method is therefore particularly effective in such a case.

Although the temporal interval between the phases P1 and P2 becomes slightly narrow as compared with the first method, overlaid views are used for the image reconstruction of the CT images at the same slice position outside the relative linear movement end point Zf at the phases P1 and P2, thereby making it possible to reduce the substitute projection data without increasing the acquired number of views and improve the quality of each CT image outside the relative linear movement end point Zf. Alternatively, the range that enables the image reconstruction can be made wide without the substitution.

Figure 11:
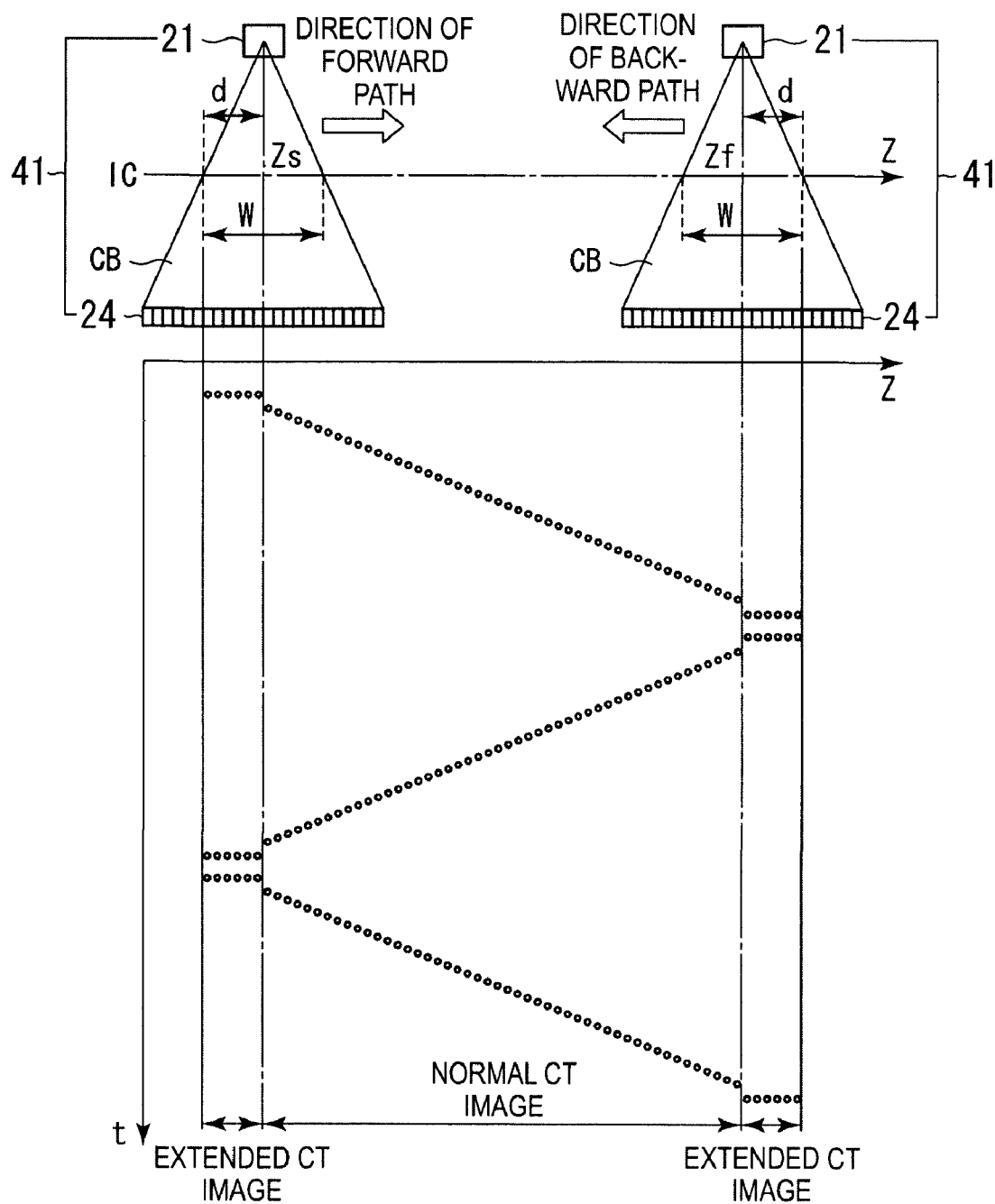
FIG. 11 is a conceptual diagram showing time and slice positions corresponding to normal CT images and extended CT images obtained where relative linear movement is shuttled repeatedly.

FIG. 11 is a conceptual diagram showing time and slice positions corresponding to normal CT images and extended CT images obtained where a relative linear movement of the X-ray data acquiring system 41 is repeated back and forth.

Thus, according to the X-ray CT apparatus 100 according to the present embodiment, CT images at slice positions lying outside a relative linear movement range are image-reconstructed using projection data in a view range equivalent to a predetermined view angle centering on a view corresponding to a relative linear movement start time or end time or its proximal view, and including each view by a resident scan and each view by a moving scan. When projection data necessary for image reconstruction lack upon the above image reconstruction, at least some of the projection data for the views by the moving scan contained in the view range are used as an alternative to the lacked projection data. Correspondingly, the view range of the projection data to be acquired by the resident scan can therefore be reduced while ensuring projection data of a view range effective in the image reconstruction by a given amount. CT images at slice positions outside a relative linear movement range at a helical scan, a helical shuttle scan, a variable-pitch helical scan, etc. can be image-reconstructed at low exposure and with high quality.

Incidentally, the above embodiment is one example of the present invention and can be changed in various ways.

The numbers of views M and N each corresponding to the amount of shift of the center view at the time that the view range used for the image reconstruction is specified, may be changed depending on the time of one rotation (one rotation time per rotation) R of the rotating section 15. For example, the numbers of views M and N may be set larger as the one rotation time R increases. Ranges suitable for the numbers of views M and N respectively correspond to, for example, the numbers of views M and N=100 to 300 views when one rotation time R=0.4 sec. assuming that the number of views corresponding to one rotation of the rotating section 15=1000, and corresponds to the numbers of views M and N=200 to 400 views when one rotation time R=0.6 sec.

The number of views M may depend on a length LS (first length) from a relative linear movement start point to an outer slice position on the side of the relative linear movement start point. The number of views N may depend on a length LF (second length) from a relative linear movement end point to an outer slice position on the side of the relative linear movement end point. For example, the number of views M may be set large as the length LS becomes large, and the number of views N may be set large as the length LF becomes large.

The number of views M and the number of views N may respectively be identical, but different in value. The number of views M corresponds to the time of acceleration of relative linear movement, and the number of views N corresponds to the time of deceleration of relative linear movement. The deceleration thereof needs control for stopping the table to a target position and has a tendency that the time required becomes long as compared with the acceleration. Therefore, the number of views N may be set smaller than the number of views M (N<M) in consideration of projection data corresponding to the more number of views being acquired in the neighborhood of a relative linear movement end point.

Incidentally, the effect of suppressing deterioration in the quality of each CT image is brought about even when the residence time t is relatively small. Consider where as shown in FIGS. 12A and 12B, for example, a view range used for image reconstruction corresponds to a view angle F (2π, for example), a view range based on a resident scan corresponds to a view angle F/2 (π, for example), and a CT image at each slice position Z7 lying within an image extension region Rf at a phase P1 is image-reconstructed. At this time, projection data PD" p1,z7,1 in the view range corresponding to the view angle F centering on a view CV1 corresponding to a relative linear movement end time at a relative linear movement end point Zf is extracted from all projection data PD" as projection data used for the image reconstruction. In doing so, the corresponding projection data are extracted so as to contain substitute projection data indicated by oblique lines as shown in FIG. 12A. Projection data corresponding to positions spaced relatively larger from the slice position Z7, i.e., projection data whose paths are spaced greatly from a path for target projection data are contained in the substitute projection data. On the other hand, although as shown in FIG. 12B, projection data PD" p1,z7,2 extracted in like manner by shifting a center view backward temporally by a view angle F/4 is approximately identical to PD" p1,z7,1 in terms of the amount of substitute projection data per se, the distance from the slice position Z7 becomes as short as about half of that in the case of PD" p1,z7,1 at the farthest position. Accordingly, the projection data extracted by the latter method becomes smaller in inconsistency at the image reconstruction and hence deterioration in the quality of each image-reconstructed CT image can be suppressed.

An X-ray CT apparatus of the present invention is available to, for example, Perfusion CT.

What is claimed is:

1. An X-ray Computed Tomography (CT) apparatus comprising:
    an X-ray tube;
    an X-ray detector comprising a plurality of detector rows;
    a rotating device configured to rotate said X-ray tube and said X-ray detector about a body axis of a subject;
    a relative linear moving device configured to relatively linearly move said X-ray tube and said X-ray detector relative to the subject from a relative linear movement start point to a relative linear movement end point;
    a scan device configured to acquire projection data by executing a resident scan and a moving scan, wherein the resident scan is for acquiring projection data while executing the rotation at at least one of the relative linear movement start point and the relative linear movement end point without executing the relative linear movement and said moving scan is for acquiring projection data while executing the rotation and the relative linear movement within a relative linear movement range; and
    an image reconstructing device configured to reconstruct CT images including at least one of a first image and a second image using the acquired projection data,
    wherein reconstruction of the first image is for reconstructing a first CT image at a first slice position located outside the relative linear movement start point of the relative linear movement range, the first CT image is reconstructed using projection data in a view range, the view range corresponding to predetermined view angles that view at the relative linear movement start time or corresponding to a proximal view being in the center thereof, and including a view based on the resident scan and a view based on the moving scan, and when projection data for the image reconstruction lack, using existing projection data based on the moving scan contained in the view range as a substitute for the lacked projection data,
    and reconstruction of the second image is for reconstructing a second CT image at a second slice position located outside the relative linear movement end point of the relative linear movement range, the second CT image is reconstructed using projection data in a view range, the view range corresponding to predetermined view angles that view at the relative linear movement end time or corresponding to a proximal view being in the center thereof, and including a view based on the resident scan and a view based on the moving scan, and when projection data for the image reconstruction lack, using existing projection data based on the moving scan contained in the view range as a substitute for the lacked projection.

2. The X-ray CT apparatus according to claim 1, wherein said scan device is configured to sequentially execute the resident scan for executing the rotation at a rotational angle smaller than the predetermined view angle at the relative linear movement start point, and the moving scan, and wherein said image reconstructing device is configured to reconstruct the first image.

3. The X-ray CT apparatus according to claim 1, wherein said scan device is configured to sequentially execute the moving scan and the resident scan for executing the rotation at a rotational angle smaller than the predetermined view angle at the relative linear movement end point, and wherein said image reconstructing device is configured to reconstruct the second image.

4. The X-ray CT apparatus according to claim 1, wherein said scan device is configured to sequentially execute the moving scan, the resident scan executes the rotation at a rotational angle smaller than twice the predetermined view angle at the relative linear movement end point, and the moving scan by setting the relative linear movement end point to a new relative linear movement start point, and wherein said image reconstructing device is configured to execute image processing using the reconstructed second image and the reconstructed first image at the new relative linear movement start point.

5. The X-ray CT apparatus according to claim 1, wherein each of the projection data used as the substitute for the lacked projection data is projection data lying in a view range of less than half the predetermined view angle.

6. The X-ray CT apparatus according to claim 1, wherein said image reconstructing device is configured to:
    reconstruct the first CT image using projection data lying in a view range centering on a view located, by a first view number, temporally prior to the view corresponding to the relative linear movement start time in reconstruction of the first image; and
    reconstruct the second CT image using projection data lying in a view range centering on a view located, by a second view number, temporally subsequent to the view corresponding to the relative linear movement end time in reconstruction of the second image.

7. The X-ray CT apparatus according to claim 6, wherein the first and second view numbers depend on one rotation time per rotation.

8. The X-ray CT apparatus according to claim 7, wherein the first and second view numbers increase as the one rotation time becomes large.

9. The X-ray CT apparatus according to claim 6, wherein the first view number depends on a first length extending from the relative linear movement start point to the slice position at the outside on the relative linear movement start point side, and wherein the second view number depends on a second length extending from the relative linear movement end point to the slice position at the outside on the relative linear movement end point side.

10. The X-ray CT apparatus according to claim 9, wherein the first view number increases as the first length becomes large, and wherein the second view number increases as the second length becomes large.

11. The X-ray CT apparatus according to claim 6, wherein the second view number is smaller than the first view number.

12. The X-ray CT apparatus according to claim 6, wherein the first and second view numbers are less than half the number of views corresponding to the predetermine view angle.

13. The X-ray CT apparatus according to claim 1, wherein the predetermined view angle is one of a p+fan angle of an X-ray beam, a 2p, and a 2p+the fan angle.

14. The X-ray CT apparatus according to claim 1, wherein a velocity of the relative linear movement changes while acquiring the projection data.

15. The X-ray CT apparatus according to claim 4, wherein each of the projection data used as the substitute for the lacked projection data is projection data lying in a view range of less than half the predetermined view angle.

16. The X-ray CT apparatus according to claim 4, wherein said image reconstructing device is configured to:
 reconstruct the first CT image using projection data lying in a view range centering on a view located, by a first view number, temporally prior to the view corresponding to the relative linear movement start time in reconstruction of the first image; and
 reconstruct the second CT image using projection data lying in a view range centering on a view located, by a second view number, temporally subsequent to the view corresponding to the relative linear movement end time in reconstruction of the second image.

17. The X-ray CT apparatus according to claim 16, wherein the first and second view numbers depend on one rotation time per rotation.

18. The X-ray CT apparatus according to claim 17, wherein the first and second view numbers increase as the one rotation time becomes large.

19. The X-ray CT apparatus according to claim 16, wherein the first view number depends on a first length extending from the relative linear movement start point to the slice position at the outside on the relative linear movement start point side, and wherein the second view number depends on a second length extending from the relative linear movement end point to the slice position at the outside on the relative linear movement end point side.

20. The X-ray CT apparatus according to claim 19, wherein the first view number increases as the first length becomes large, and wherein the second view number increases as the second length becomes large.

* * * * *

UNITED STATES PATENT AND TRADEMARK OFFICE
CERTIFICATE OF CORRECTION

PATENT NO. : 8,358,824 B2  
APPLICATION NO. : 12/652634  
DATED : January 22, 2013  
INVENTOR(S) : Hagiwara Page 1 of 1

It is certified that error appears in the above-identified patent and that said Letters Patent is hereby corrected as shown below:

In the Drawings

In Fig. 5, Sheet 5 of 12, for Tag "B3", in Line 2, delete "(RECONSTRCUTION" and insert -- (RECONSTRUCTION --, therefor.

In the Specifications

In Column 5, Line 44, delete "time t" and insert -- time $\tau$ --, therefor.

In Column 5, Line 46, delete "time t" and insert -- time $\tau$ --, therefor.

In Column 9, Line 61, delete "to to" and insert -- t0 to --, therefor.

In Column 14, Line 61, delete "time t" and insert -- time $\tau$ --, therefor.

Signed and Sealed this  
Fourth Day of June, 2013

Teresa Stanek Rea  
*Acting Director of the United States Patent and Trademark Office*